US006739207B2

(12) United States Patent
Sjöquist (10) Patent No.: US 6,739,207 B2
(45) Date of Patent: May 25, 2004

(54) GRINDING AND SAMPLE PRESENTATION FOR ANALYSIS

(75) Inventor: Anders Sjöquist, Höganäs (SE)

(73) Assignee: Foss Tecator AB, Hoganas (SE)

( * ) Notice: Subject to any disclaimer, the term of this patent is extended or adjusted under 35 U.S.C. 154(b) by 0 days.

(21) Appl. No.: 10/283,122

(22) Filed: Oct. 30, 2002

(65) Prior Publication Data

US 2004/0000202 A1 Jan. 1, 2004

(30) Foreign Application Priority Data

Jun. 28, 2002 (SE) .............................................. 0202011

(51) Int. Cl.⁷ ................................................. G01N 1/00
(52) U.S. Cl. .................................................. 73/864.81
(58) Field of Search ...................... 73/866, 863, 864.81; 250/339.1, 339.11, 339.12, 339.14, 341.8, 358.1

(56) References Cited

U.S. PATENT DOCUMENTS

| 4,400,086 A | 8/1983 | Webster | |
|---|---|---|---|
| 4,800,280 A | 1/1989 | Satake | |
| 4,951,887 A | * 8/1990 | Gutnecht | 241/260.1 |
| 5,058,444 A | * 10/1991 | Anthony et al. | 73/866 |
| 5,183,215 A | * 2/1993 | Getzmann | 241/62 |
| 5,212,994 A | * 5/1993 | von Alfthan et al. | 73/866 |
| 5,700,961 A | * 12/1997 | Anthony et al. | 73/866 |
| 5,834,661 A | * 11/1998 | Nonaka et al. | 73/866 |
| 6,020,588 A | * 2/2000 | Ditmarsen et al. | 250/339.12 |

FOREIGN PATENT DOCUMENTS

| DE | 3441856 | 10/1985 |
|---|---|---|
| EP | 0365205 | 4/1990 |

* cited by examiner

Primary Examiner—Robert Raevis
(74) Attorney, Agent, or Firm—Harness, Dickey & Pierce, PLC (57) ABSTRACT

A device and a method for combined selection of a sample, grinding of the selected sample and presentation of the sample for an analysis system. The device includes a grinding chamber, a grinding device for grinding said sample in the grinding chamber, and a pressing device for compression of the sample in and output of the sample from the grinding chamber. The device further includes a first chamber opening for input of the sample into the grinding chamber, and a second chamber opening for the output of the sample from the grinding chamber, wherein the first chamber opening is separate from the second chamber opening.

23 Claims, 7 Drawing Sheets

GRINDING AND SAMPLE PRESENTATION FOR ANALYSIS

The present application hereby claims priority under 35 U.S.C. §119 on Swedish patent application number SE 0202011-3 filed Jun. 28, 2002, the entire contents of which are hereby incorporated herein by reference.

TECHNICAL FIELD OF THE INVENTION

The present invention generally relates to a device and a method for combined selection of a sample, grinding of the selected sample and presentation of the sample for an analysis system.

BACKGROUND OF THE INVENTION

A device according to above is previously known. Such a device is used to facilitate spectrometric analysis of a product sample, consisting of e.g. pasta, grain, other feedstuff, or industrial material components, which should be grinded before the analysis. The selection of the sample may be made directly from a process line (On-Line analysis sampling). Common types of spectrometric analyses which may be used are Near Infrared Reflection (NIR) and Near Infrared Transmission (NIT) analysis.

The previously known device comprises a combined sample container and grinding chamber. In the grinding chamber, a plunger is arranged which encompasses a rotatable and axially movable knife rotor. The axis of the knife rotor extends parallell to the axis of the grinding chamber. To the knife rotor, a number of knives are attached.

The grinding chamber of the previously known device is arranged on an external rotor which is positioned in a stator. The stator is in turn arranged where the samples are to be selected. On the stator is a presentation matrix arranged, into which the sample may be pressed out from the grinding chamber for analysis through a window of the presentation matrix.

When using the previously known device, the sample is first taken from the process line to the grinding chamber through an open end of the chamber. Then the rotor is turned to a position where the open end of the grinding chamber is covered by the stator, and the knife rotor is moved backwards and forwards in the chamber for grinding the sample. After that, the rotor is turned further to an analysis position where the grinded sample is pressed by the plunger into the presentation matrix for analysis. After the analysis, the sample is pressed out from the device through the presentation matrix.

The previously known device allows sample selection, grinding and presentation for an analysis system to be combined in one single unit. This gives a lot of advantages compared to other prior art, where the product sample is taken through several part processes in different units in order to be analysed. Examples of problems known from other prior art which may be eliminated by using the previously known device are: contamination of samples, cleaning up remains from earlier samples in several units, and expensive and complicated transport systems to transport samples from the process line to an analysis central and back again.

However, the previously known device has also a few disadvantages. The construction with rotor and stator, for shifting between positions for sample selection, grinding and analysis, is relatively complicated and bulky.

The previously known device may also be utilized without the rotor and stator by enclosing the grinding chamber manually with a lid. The lid may after grinding optionally be replaced by a presentation matrix for analysis of the sample. A disadvantage with this solution is, however, that it is manual and therefore only is practically usable for occasional samples.

SUMMARY OF THE INVENTION

An object of an embodiment of the present invention is to provide an improved device and method for combined selection of a sample, grinding of the selected sample and presentation of the sample for an analysis system.

Another object of an embodiment of the present invention is to further develop the basic idea of the previously known device described above into a simplifyed and rationalized device.

Preferably, an embodiment of the present invention shall also enable improved repeatability of the analysis conditions from one sample analysis to another.

For achieving at least some of these and other objects, a device and a method according to an embodiment of the invention are provided.

More particularly, according to an embodiment of the invention, a device for combined selection of a sample, grinding of the selected sample and presentation of the sample for an analysis system, comprises a grinding chamber, a grinding means for grinding said sample in said grinding chamber, and a pressing means for compression of said sample in and output of said sample from said grinding chamber. The device is characterized in that it further comprises a first chamber opening for input of said sample into said grinding chamber, and a second chamber opening for said output of said sample from said grinding chamber, wherein said first chamber opening is separate from said second chamber opening. By having one chamber opening for input of the sample and another chamber opening for output of the sample, the need for turning the grinding chamber and thereby also the need for a rotor and a stator is eliminated.

By eliminating the need for turning the grinding chamber, another advantage is also gained. Turning of the grinding chamber increases the segregation between small and large particles of the sample material, which results in that the presented sample becomes inhomogeneous. This deteriorates the analysis result, wherefore elimination of the need for turning the grinding chamber is advantageous.

As defined herein, "grinding" means transformation of the material into smaller particles. Hence, grinding also includes atomization or pulverization of a solid material, as well as coarse grinding. The grinding may be accomplished by means of cutting, milling, or some other process.

In one embodiment of the invention, said second chamber opening is arranged to be closed during said compression of said sample. This makes it possible to achieve controllable compression of the sample for analysis. Controllable compression makes it possible to accomplish similar analysis conditions from one sample analysis to another. This improves the repeatability and comparability between different sample analyses.

Especially when spectrum analysis, such as NIR or NIT analysis, is used, it is important to control the compression of the sample, since different compressions result in different spectra. The only interesting parameter for spectral analysis is the spectra of the sample material, wherefore the influence or variation of all other parameters, including compression of the sample, particle size (degree of grinding of the material), air pressure, heat, moisture etc, must be reduced as much as possible. The previously known device described above comprises a presentation matrix with a smaller diameter then the grinding chamber of the device. A sample is pressed from the grinding chamber into this presentation matrix, whereby a certain small compression of the sample for analysis is achieved. However, a drawback with this solution is that the presentation matrix is open in the outer end, wherefore controllable compression of the sample is not possible.

In another embodiment of the invention, the device is arranged so that said sample is inside said grinding chamber during said presentation of said sample for the analysis system. This eliminates the need for a separate presentation matrix, which is used in the previously known device, and contributes to further decrease of the above mentioned segregation of the sample particles.

In another embodiment of the invention, said second chamber opening is arranged to be closed during said presentation of said sample for the analysis system. This is another feature which adds to decreased segregation of the sample particles and repeatable analysis conditions.

In another embodiment, said first chamber opening is arranged to be closed during said compression of said sample. Depending on the actual construction of the grinding chamber, a closed first chamber opening during the compression further facilitates controllable compression.

In yet another embodiment of the invention, said pressing means is arranged to compress said sample to a predetermined compression for said presentation for the analysis system. This makes it possible to minimize the variations in compression between different samples. As explained above, variations in the compression affects the result of a spectral analysis.

In another embodiment, said pressing means is arranged to automatically stop compressing said sample at a predetermined counter force from the sample. Automatic stop of the compression increases the efficiency and reliability of the process. The counter force from the sample could for example be measured by means of a pressure sensor of the pressing means or by means of a voltage or current gauge at a motor which drives the pressing means.

In another embodiment, said compression of said sample by said pressing means is accomplished by means of a compressed-air device to which the pressing means is connected. The use of a compressed-air device is advantageous since with such a device, the same compression may be achieved, from one sample analysis to another, irrespective of the size of the sample. This is because the magnitude of the compression is determined by the air pressure of the compressed-air device.

In yet another embodiment, said pressing means is arranged to compress said sample essentially perpendicularly against an analysis window for said presentation for the analysis system. An advantage with this is that the compression may be made more homogeneous over the whole sample, in order to further improve the controllability of the compression.

According to another embodiment of the invention, a second closing means which is arranged for closing said second chamber opening comprises said analysis window. Thereby both the compression of the sample towards the analysis window for the analysis and the output of the sample from the grinding chamber may be made in the same direction by means of the pressing means.

According to another embodiment, said second closing means is movable away from said second chamber opening. This makes it possible to output the sample from the grinding chamber.

According to what is previously known, output of a sample from the known device is made by pressing, by means of a plunger, the sample from the corresponding grinding chamber, through a presentation matrix with a smaller diameter than the grinding chamber, out to the open air. This plunger stops pushing the sample at the end of the grinding chamber, wherefore a piece of the sample is left inside the presentation matrix after the output. When a new sample analysis is to be made, the left old sample piece is supposed to be pushed out from the presentation matrix by the new sample being pressed into the presentation matrix. However, this solution is disadvantageous since there is no guarantee that all rests of the old sample piece are pushed out. Some rests may be stuck inside the presentation matrix, for example on the analysis window, which may contaminate the new sample and deteriorate the result of the new sample analysis. Especially if a long time has elapsed between the sample analyses, the old sample piece may have dryed and got firmly stuck to the analysis window.

According to another embodiment of the invention, said pressing means is movable at least as far as to the plane of said second chamber opening. This makes it possible to output the whole sample from the device, without leaving any piece of the sample inside the device.

According to yet another embodiment, said second closing means is movable in the plane of said second chamber opening. In the case when the closing means comprises the analysis window, this embodiment makes it possible to arrange so that remains from the sample are wiped off the analysis window automatically when the closing means is opened for output of the sample from the grinding chamber. With the previuosly known device, the "automatic wiping" is made only by new sample material being pushed parallell against the corresponding analysis window, which is not an efficient and reliable method.

In an alternative embodiment of the invention, said second closing means is movable perpendicularly to the plane of said second chamber opening. This embodiment is suitable if manual cleaning of the analysis window is preferred.

In another embodiment of the invention, said first chamber opening is arranged to be closed by means of a first closing means which is movable in the plane of said first chamber opening. This makes it possible to arrange the device with its first chamber opening directly adjacent to a process line, from which samples are taken into the grinding chamber through the first chamber opening.

In yet another embodiment of the invention, said first chamber opening is arranged for input of said sample essentially perpendicularly in relation to the direction of said compression of said sample. This facilitates a simple construction of the device.

In a further embodiment of the invention, said device is arranged to present said sample for a Near Infrared Reflection analysis system, which is a well established analysis method within e.g. the food industry.

In another embodiment, said device is arranged to present said sample for a Near Infrared Transmission analysis system, which is another similar well established analysis method.

According to the invention, a method for combined selection of a sample, grinding of the selected sample and presentation of the sample for an analysis system, comprises the following. Input of said sample into a grinding chamber through a first chamber opening, grinding of said sample in said grinding chamber, compression of said grinded sample in said grinding chamber, presentation of said grinded and compressed sample in said grinding chamber for an analysis system, and output of said sample from said grinding chamber through a second chamber opening, wherein said second chamber opening is separate from said first chamber opening.

According to one embodiment of the invention, said second chamber opening is closed during said compression of said grinded sample.

According to another embodiment of the invention, said compression of said grinded sample is made to a predetermined compression for said presentation for the analysis system.

According to another embodiment, said compression of said grinded sample stops automatically at a predetermined counter force from the sample.

According to yet another embodiment, said compression of said grinded sample is made essentially perpendicularly against an analysis window for said presentation.

In another embodiment of the invention, said presentation is made for a Near Infrared Reflection analysis system.

In yet another embodiment of the invention, said presentation is made for a Near Infrared Transmission analysis system.

BRIEF DESCRIPTION OF THE DRAWINGS

The present invention will now be described in more detail with reference to the accompanying drawings, in which.

DETAILED DESCRIPTION OF PREFERRED EMBODIMENTS

Figure 1:
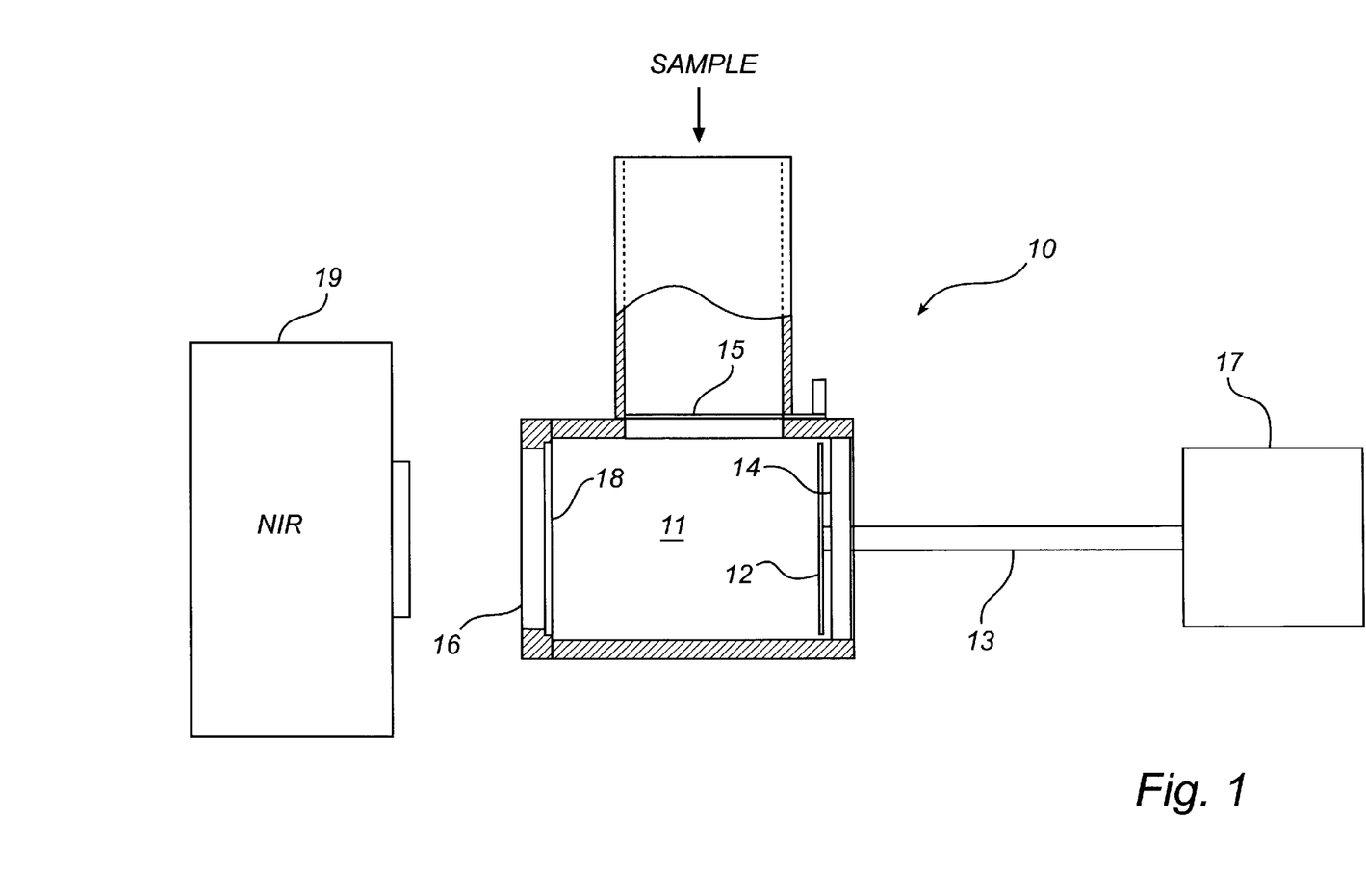
FIG. 1 is a schematic view of one embodiment of a device according to the invention.

FIG. 1 shows one embodiment of a device 10 according to the invention. The device 10 comprises a grinding chamber 11, a grinding means, here in the form of a number of knives 12 arranged on a rotatable and axially movable rotor 13, for grinding a sample of a material in the grinding chamber 11, and a pressing means, here in the form of a plunger 14 which encompasses the rotor 13, for compression of the sample in and output of the sample from the grinding chamber 11. The axis of the rotor 13 extends parallell to the longitudinal axis of the grinding chamber 11.

The device 10 further comprises a first chamber opening for input of the sample into the grinding chamber 11, and a second chamber opening for output of the sample from the grinding chamber 11. A first closing means, here in the form of a sliding lid 15, is arranged for covering the first chamber opening, and a second closing means, here in the form of a cover 16 which is movable perpendicularly to the plane of the second chamber opening, is arranged for covering the second chamber opening.

A motor 17 is arranged to rotate the rotor 13 with the knives 12, and a compression means (not shown), for example a compressed-air device, is arranged to press the plunger 14 against the sample for compression and output of the sample from the grinding chamber 11. A second motor (not shown), is also arranged for moving the rotor 13 with the knives 12 and the motor 17 backwards and forwards in the grinding chamber 11. Alternatively, the functions of the compression means and the second motor may be provided by one single motor unit.

In the second closing means, an analysis window 18 is arranged for presentation of the sample for an analysis system, here a NIR (Near Infrared Reflection) analysis system 19, which analyses the light that is reflected from the sample material back to the NIR analysis system 19.

Figure 3:
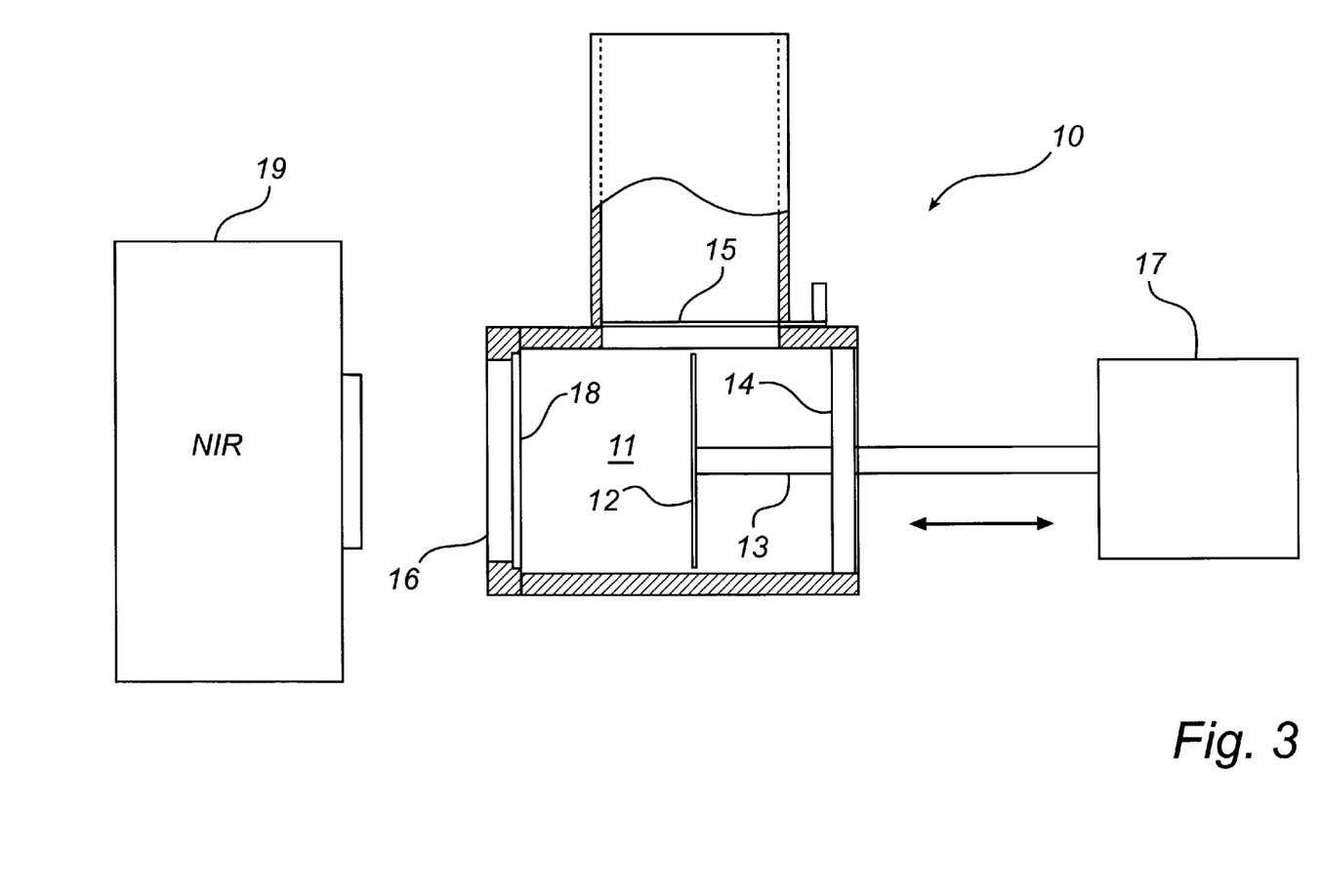
FIG. 3 is a schematic view illustrating grinding of a selected sample using the device shown in FIG. 1.
Figure 4:
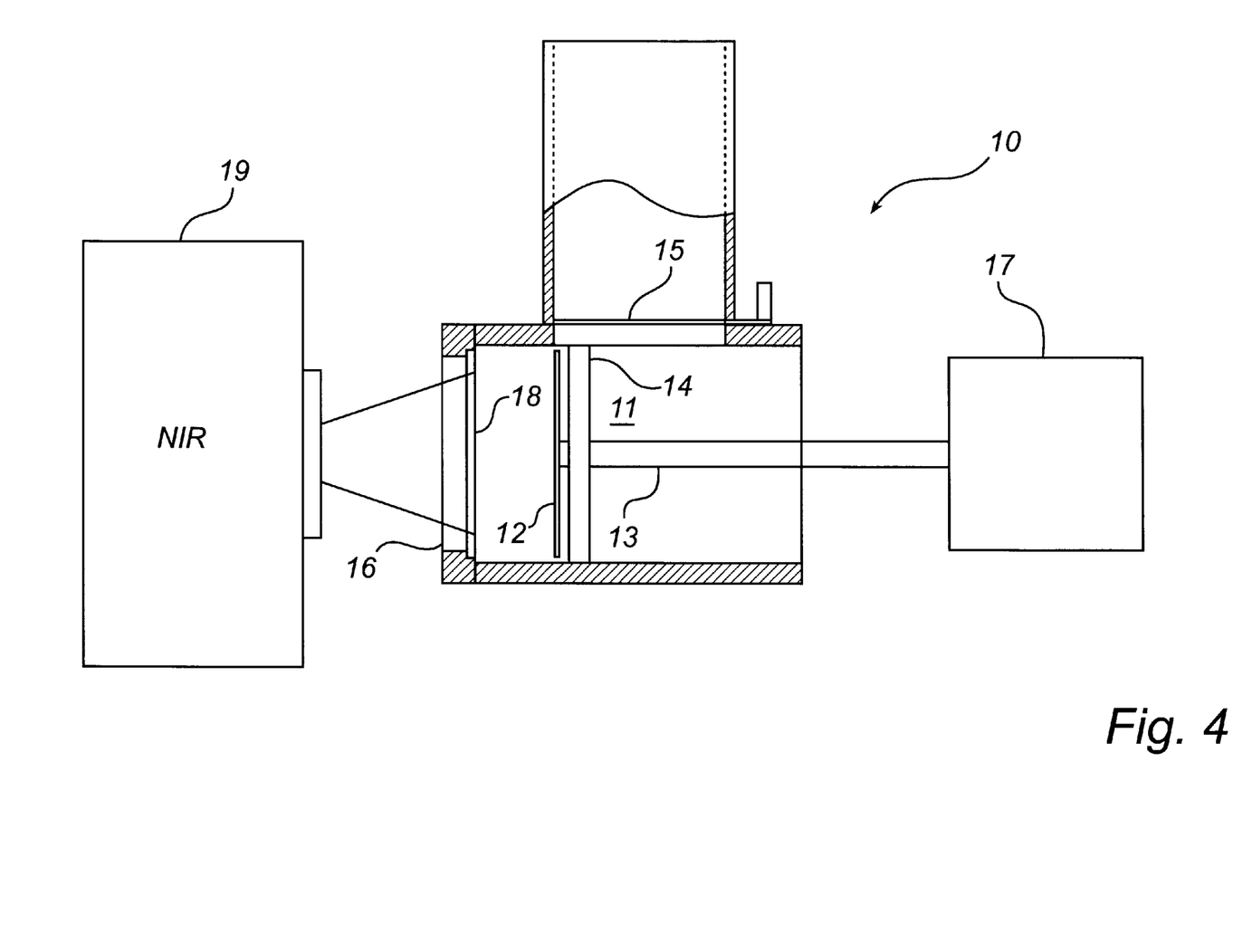
FIG. 4 is a schematic view illustrating compression and presentation of a sample for a NIR analysis system using the device shown in FIG. 1.
Figure 5:
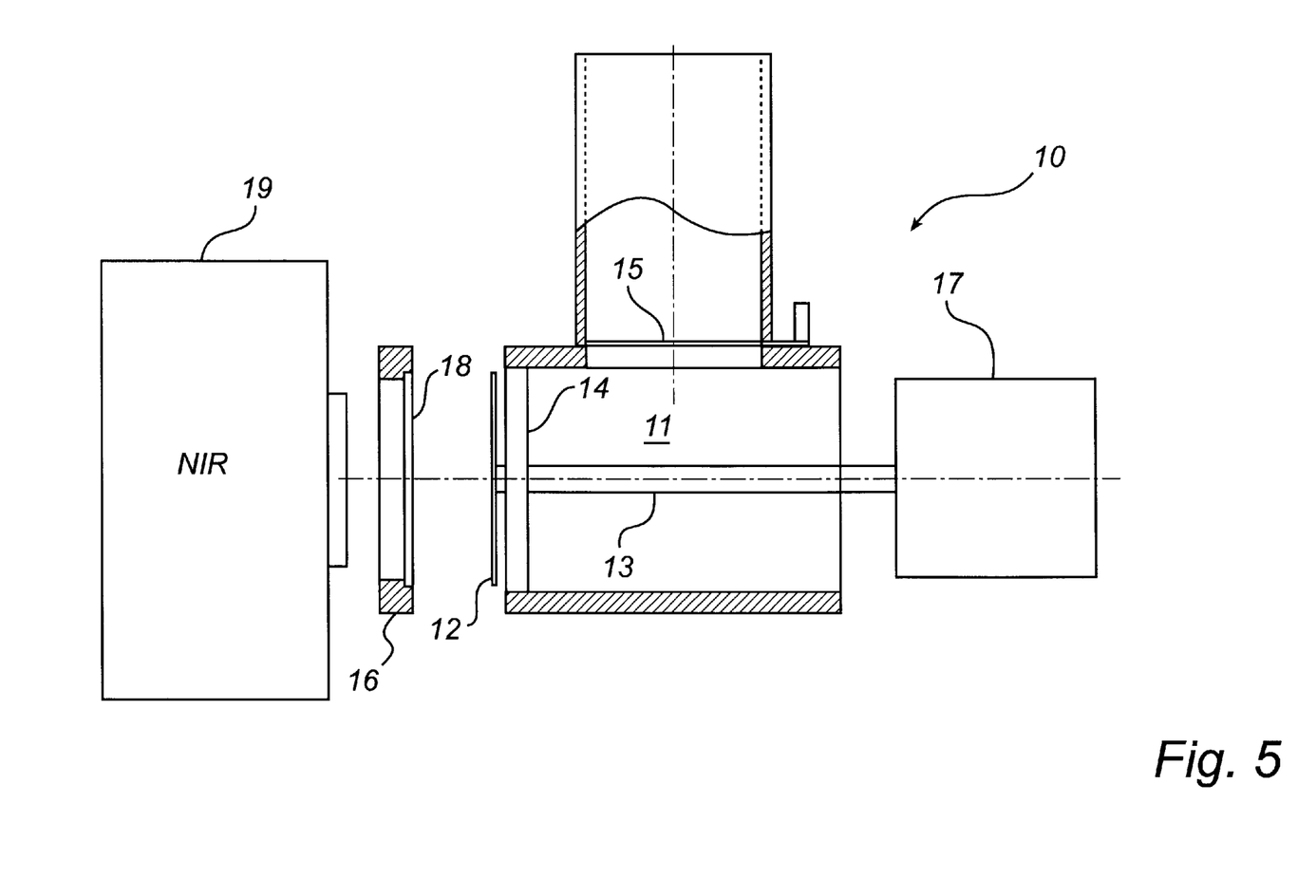
FIG. 5 is a schematic view illustrating output of a sample from the device shown in FIG. 1.

FIGS. 2 to 5 show the use of the device in FIG. 1 for combined selection of a sample (FIG. 2), grinding of the selected sample (FIG. 3), and presentation of the sample for the analysis system 19 (FIG. 4), whereafter the sample is outputted from the grinding chamber 11 (FIG. 5).

Figure 2:
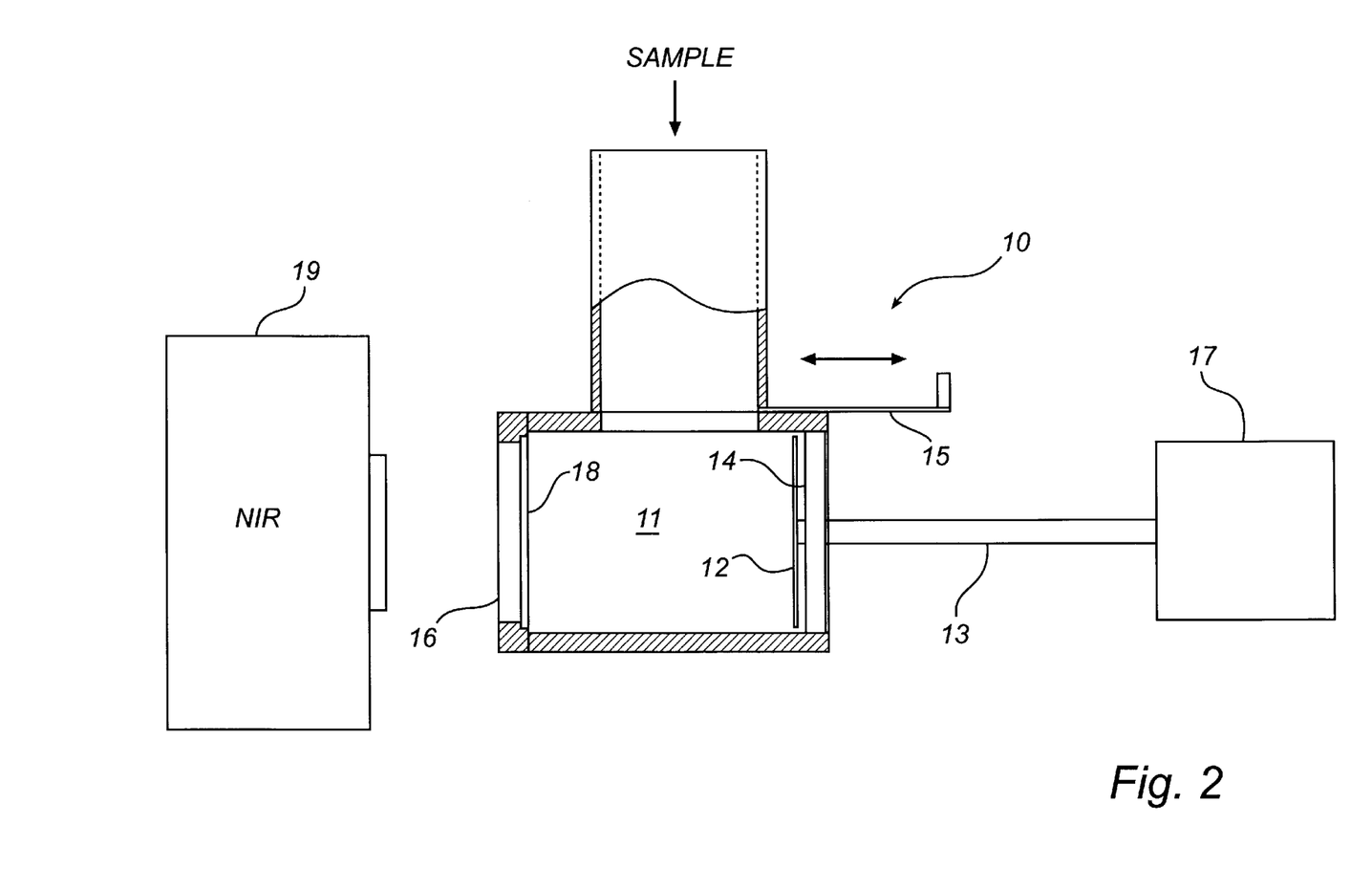
FIG. 2 is a schematic view illustrating selection of a sample to the device shown in FIG. 1.

In FIG. 2 is illustrated how the sample, for example directly from a process line, is taken into the grinding chamber 11 by opening of the sliding lid 15. When the sliding lid 15 is moved parallell to the plane of the first chamber opening and uncovers this opening, the sample will fall into the grinding chamber 11 by means of the gravity. After the input of the sample to the grinding chamber 11, the first chamber opening is closed.

The material of the sample is streamable but not liquid. Examples of materials to which the device 10 is applicable are pasta, grain and other feedstuff, or industrial material components such as pellets and other plastics.

The first closing means, here the sliding lid 15, may be specially designed so that sample material not happen to get stuck between the first closing means and the rim of the first chamber opening. For example, the sliding lid 15 may be provided with a sharp edge which cuts pieces of material that have been jammed between the sliding lid 15 and the rim of the first chamber opening.

FIG. 3 shows grinding of the sample, which in FIG. 2 was taken into the grinding chamber 11. The sample is grinded by means of the grinding means, here the rotating knives 12 on the rotor 13, which is moved backwards and forwards in the grinding chamber 11 by means of the second motor.

The degree of grinding of the material is determined by the rotation speed of the knives 12 and by the number of times that the knives 12 are moved backwards and forwards in the grinding chamber 11.

FIG. 4 shows compression of the grinded sample and presentation of the grinded sample for the analysis system 19. The pressing means, here the plunger 14 with the knives 12 in front of it, driven by the compression means, compresses the sample material against the analysis window 18 in order to achieve a good presentation of the sample for the analysis system. The compression of the sample is here made essentially perpendicularly against the analysis window so that the compression of the sample material becomes more homogeneous. The plunger 14 is preferably arranged such that air is allowed to leak over from the decreasing space for the sample to the other side during the compression, in order to maintain the same air pressure around the sample to be analysed.

The degree of compression may be predetermined so that similar analysis conditions, in terms of compression of the sample material and amount of air between the pieces of sample material, are achieved for different sample analyses. The second motor may hereby be arranged to automatically stop pressing the plunger 14 against the sample at a predetermined counter force from the sample. The counter force from the sample may for example be measured by means of a pressure sensor (not shown) arranged on the plunger 14 or by means of a voltage or current gauge at the compression means which drives the plunger 14.

When the sample is compressed to the predetermined compression, spectral analysis with the NIR analysis system 19 of the sample is performed through the analysis window 18.

FIG. 5 shows output of the sample from the grinding chamber 11 after the compression and presentation of the sample for the analysis system. The sample is output by opening of the second closing means, here the cover 16 with the analysis window 18, and movement of the plunger 14 forward to the second chamber opening so that the sample is pushed out from the grinding chamber 11.

The output sample may be collected for further analysis or for recycling back to the process line.

After the output of the sample from the grinding chamber 11 and while the second chamber opening still is open, the analysis window 18 may be cleaned if it is contaminated with sample material.

Figure 6:
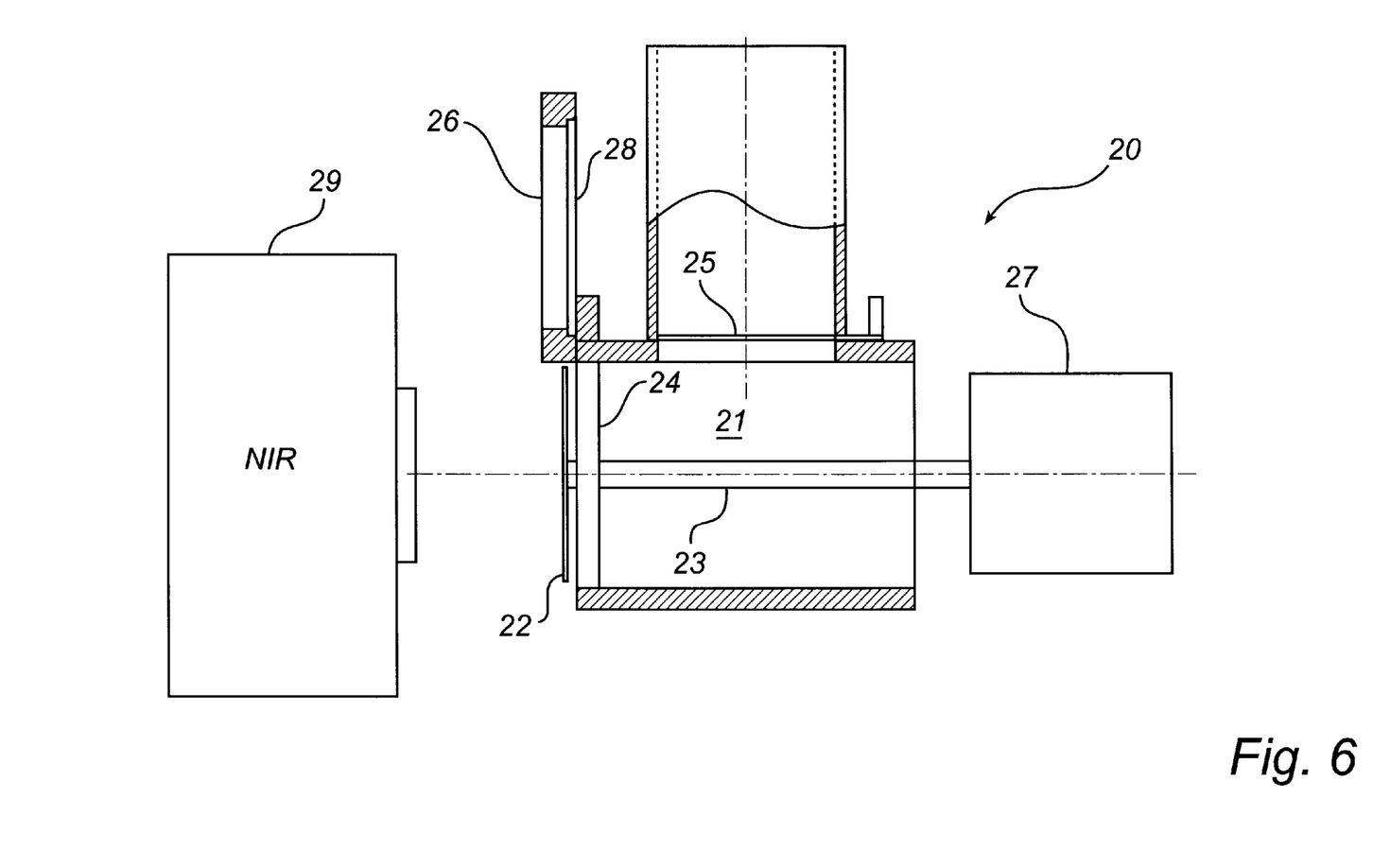
FIG. 6 is a schematic view of another embodiment of a device according to the invention.

FIG. 6 shows an alternative embodiment of a device 20 according to the invention which is able to automatically clean the analysis window 28 after presentation of a sample for an analysis system 29. The device 20 comprises, just like the device 10 in FIGS. 1 to 5, a rotor 23, driven by a motor 27, knives 22 arranged on the rotor 23 for grinding the sample inside a grinding chamber 21, and a plunger 24 for compression and output of the sample from the grinding chamber 21. The device also comprises a first chamber opening which may be covered by a first closing means, here a sliding lid 25, and a second chamber opening which may be covered by a second closing means, here a cover 26 comprising the analysis window 28.

The difference compared to the device 10 is that the cover 26 is movable in the plane of the second chamber opening, so that remains from the sample may be wiped off the analysis window 28 automatically against the rim of the second chamber opening when the cover 26 is opened for output of the sample from the grinding chamber 21.

Figure 7:
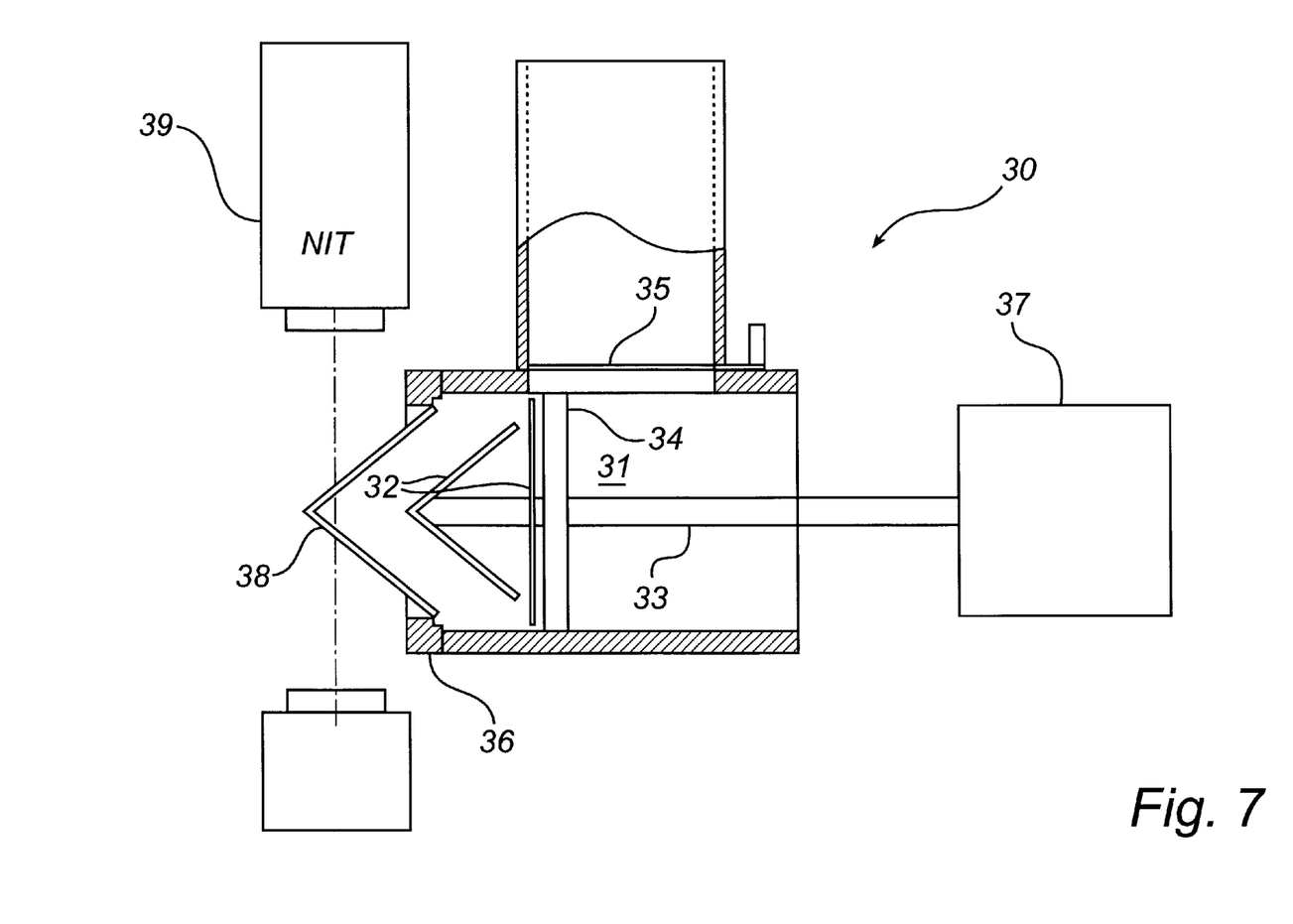
FIG. 7 is a schematic view of yet another embodiment of a device according to the invention.

FIG. 7 shows another embodiment of a device 30 according to the invention, where a NIT (Near Infrared Transmission) analysis system 39 may be used for analysis of a sample presented by the device 30. When NIT analysis is used, the light that is transmitted through the sample material is analysed.

This device 30 comprises, like the device shown in FIGS. 1 to 5 and the device shown in FIG. 6, a grinding chamber 31, knives 32, a rotor 33, a plunger 34, a sliding lid 35, a cover 36, a motor 37, and an analysis window 38. The difference is that in this embodiment, the analysis window 38 is wedge-shaped in the direction out from the grinding chamber 31, so that NIT analysis may be performed perpendicularly to the direction of the compression of the sample. Because the analysis window 38 is wedge-shaped, the shape of the knives 32 is modified so that the whole grinding chamber 31 may be reached by the rotating knives 32.

A special advantage with this construction is that the NIT analysis system 39 may simply be moved parallell to the direction of the axis of the rotor 33 in order to change the distance that the light travels through the sample material.

The NIR and NIT analysis systems used together with the above described embodiments work with infrared light. However, the invention may be used for analysis within other parts of the electromagnetic frequency spectrum as well.

Further, the device according to the invention may also be used for sample preparation before other analyses than spectral analyses, like for example chemical analyses.

It is to be understood that modifications of the above described systems and methods can be made by people skilled in the art without departing from the spirit and scope of the invention.

What is claimed is:

1. A device for use in a spectrophotometric analysis system, the device comprising:
    a grinding chamber,
    a grinding means for grinding said sample in said grinding chamber,
    a pressing means for compression of said sample in and output of said sample from said grinding chamber,
    a first chamber opening for input of said sample into said grinding chamber,
    a second chamber opening for said output of said sample from said grinding chamber,
    wherein said first chamber opening is separate from said second chamber opening, and
    wherein the device is arranged so that said sample is inside said grinding chamber during said presentation of said sample to the analysis system.

2. A device according to claim 1, wherein said second chamber opening is arranged to be closed during said compression of said sample.

3. A device according to claim 1, wherein said second chamber opening is arranged to be closed during said presentation of said sample to the spectrophotometric analysis system.

4. A device according to claim 1, wherein said first chamber opening is arranged to be closed during said compression of said sample.

5. A device according to claim 1, wherein said pressing means is arranged to compress said sample to a predetermined compression for said presentation to the stpectrophotometric analysis system.

6. A device according to claim 1, wherein said pressing means is arranged to automatically stop compressing said sample at a predetermined counter force from the sample.

7. A device according to claim 1, wherein said pressing means is arranged to compress said sample essentially perpendicularly against an analysis window for said presentation to the spectrophotometric analysis system.

8. A device according to claim 1, wherein a closing means which is arranged for closing said second chamber opening comprises said analysis window.

9. A device according to claim 8, wherein said closing means is movable away from said second chamber opening.

10. A device according to claim 8, wherein said closing means is movable in the plane of said second chamber opening.

11. A device according to claim 8, wherein said closing means is movable perpendicularly to the plane of said second chamber opening.

12. A device according to claim 1, wherein said pressing means is movable at least as far as to the plane of said second chamber opening.

13. A device according to claim 1, wherein said first chamber opening is arranged to be closed by means of a first closing means which is movable in the plane of said first chamber opening.

14. A device according to claim 1, wherein said first chamber opening is arranged for input of said sample essentially perpendicularly in relation to the direction of the compression of said sample.

15. A device according to claim 1, wherein said device is arranged to present said sample to a Near Infrared Reflection analysis system.

16. A device according to claim 1, wherein said device is arranged to present said sample to a Near Infrared Transmission analysis system.

17. A method for grinding a sample and presenting the sample to a spectrophotometric analysis system, said method comprising:

inputting said sample into a grinding chamber through a first chamber opening, grinding said sample in said grinding chamber, compressing said grinded sample in said grinding chamber, presenting said grinded and compressed sample in said grinding chamber to said spectrophotometric analysis system, and outputting said sample from said grinding chamber through a second chamber opening, wherein said second chamber opening is separate from said first chamber opening.

18. A method according to claim 17, wherein said second chamber opening is closed during said compression of said grinded sample.

19. A method according to claim 17, wherein said compression of said grinded sample is made to a predetermined compression for said presentation the spectrophotometric analysis system.

20. A method according to claim 17, wherein said compression of said grinded sample stops automatically at a predetermined counter force from the sample.

21. A method according to claim 17, wherein said compression of said grinded sample is made essentially perpendicularly against an analysis window for said presentation.

22. A method according to claim 17, wherein said presentation is made to a Near Infrared Reflection analysis system.

23. A method according to claim 17, wherein said presentation is made to a Near Infrared Transmission analysis system.

* * * * *